United States Patent [19]

Pohndorf et al.

[11] Patent Number: 5,324,321

[45] Date of Patent: Jun. 28, 1994

[54] MEDICAL ELECTRICAL LEAD HAVING SIGMOIDAL CONDUCTORS AND NON-CIRCULAR LUMENS

[75] Inventors: Peter J. Pohndorf, Stillwater; Joseph F. Lessar, Coon Rapids; James E. Upton, New Brighton; Kenneth E. Cobian, St. Anthony, all of Minn.

[73] Assignee: Medtronic, Inc., Minneapolis, Minn.

[21] Appl. No.: 994,755

[22] Filed: Dec. 22, 1992

[51] Int. Cl.$^5$ ............................................. A61N 1/04
[52] U.S. Cl. .................................................. 607/116
[58] Field of Search ................................ 128/784–788, 128/642

[56] References Cited

U.S. PATENT DOCUMENTS

| | | | |
|---|---|---|---|
| 3,333,045 | 7/1967 | Fisher et al. | 128/784 |
| 3,348,548 | 10/1967 | Chardack | 128/784 |
| 3,416,533 | 12/1968 | Fisher et al. | 607/116 |
| 3,416,534 | 12/1968 | Quinn | 607/116 |
| 3,788,329 | 1/1974 | Friedman | 607/116 |
| 3,865,118 | 2/1975 | Bures | 128/786 |
| 3,995,623 | 12/1976 | Blake et al. | 128/642 |
| 4,106,512 | 8/1978 | Bisping | 607/116 |
| 4,198,961 | 4/1980 | Harris | 128/784 |
| 4,328,806 | 5/1982 | Cooper | 128/786 |
| 4,369,794 | 1/1983 | Furler | 128/642 |
| 4,394,866 | 7/1983 | Hughes | 128/786 |
| 4,411,277 | 10/1983 | Dickhudt | 128/784 |
| 4,553,554 | 11/1985 | Lemole | 128/784 |
| 4,606,017 | 7/1986 | Schroeppel | 128/784 |
| 4,608,986 | 9/1986 | Beranek | 128/786 |
| 4,759,378 | 7/1988 | Swendson et al. | 128/786 |
| 4,945,342 | 7/1990 | Steinemann | 128/784 |
| 4,947,866 | 8/1990 | Lessar et al. | 128/784 |

OTHER PUBLICATIONS

Advertisement in Medical Product Manufacturing News, Jul./Aug., 1990 by Putnam Plastics Corporation.

*Primary Examiner*—William E. Kamm
*Attorney, Agent, or Firm*—Reed A. Duthler; Harold R. Patton

[57] ABSTRACT

An implantable lead including one or more sigmoidal or serpentine shaped conductors which are placed in one or more lumens formed in and extending along the length of the lead body. The conductor is shaped with its undulating curve lying generally in one plane. The lumen in cross section is greater in width than in height. The sigmoidal conductor extends along the length of the lead body and across the width of the lumen.

17 Claims, 1 Drawing Sheet

MEDICAL ELECTRICAL LEAD HAVING SIGMOIDAL CONDUCTORS AND NON-CIRCULAR LUMENS

BACKGROUND OF THE INVENTION

The present invention relates to a lead for use with an implantable medical device. More particularly, the invention relates to a multiple lumen, multiple conductor, pacemaker lead.

Permanently implantable electrical lead systems are used in conjunction with implantable medical devices, such as pacemakers, nerve and muscle stimulators and anti-tachycardia devices. In these applications the lead is used to transmit electrical signals to and/or from the medical device. Leads of this type may be chronically implanted and are expected to exhibit a long service life in a hostile environment of the human body.

The traditional lead includes a lead body having a generally circular exterior cross-section and one or more circular lumens, which may be arranged coaxially or parallel to one another. Typically, spiral wound metallic conductors are positioned within one or more lumens of the lead body. The spiral wound conductor also forms a lumen which can receive a stylet to help stiffening the lead as an aid to lead placement during lead implantation.

Alternative conductor designs have been proposed in the context of implantable multiple lumen multiple conductor leads. U.S. Pat. No. 4,608,986 issued to Beranek discloses a round lead having an array of round lumens. This lead places a single "straight" strand of metallic conductor loosely into each lumen. An exotic metal formulation is stated to avoid the problems of breakage due to flexing normally associated with straight conductors. An additional alternative conductor for use in implantable leads is bundled, stranded wire, as disclosed in U.S. Pat. No. 4,964,414, issued to Handa et al.

SUMMARY OF THE INVENTION

The implantable lead of the present invention includes one or more sigmoidal or serpentine conductors which are placed in one or more non-round lumens formed in and extending longitudinally along the length of the lead body. The conductor is sigmoidal or serpentine, with the undulating curve of each such conductor lying generally in one plane. In a preferred embodiment, the conductors each take the form of bundled strands of extremely small diameter wire.

The "non-round" lumen shape is broader in a first dimension, (hereafter referred to as "width") than in a second dimension perpendicular thereto (hereafter referred to as "height"). In cross section, the lumen shape is thus somewhat flattened, with areas of generally less curvature extending across the width of the lumens connected to one another by areas of greater curvature (hereafter referred to as "edges"). In a preferred embodiment, the lumen's height is greater in cross section in the region between its edges and less in regions adjacent its edges.

Each conductor is located in a lumen such that the plane in which its undulations lie generally extends across the width of the lumen. In embodiments having reduced lumen thicknesses adjacent the edges, the areas of contact between the conductor and the inner surface of the lumen will be limited to the regions adjacent the edges.

In some embodiments, plural, non-circular lumens are arranged so that their width extends generally perpendicular to a radius of the lead body and/or generally parallel to the outer surface of the lead body. A conventional round lumen may be optionally included in the lead body as well. This round lumen will typically contain a conventional spiral wound conductor, to provide a stylet receiving lumen.

Leads made in accordance with this invention are extremely flexible and, unlike leads employing straight conductors as discussed above, can be stretched while in use. Leads according to the present invention are believed to exhibit improved crush resistance as compared to leads having similar sizes and numbers of conductors manufactured in more conventional round coil and lumen configurations. Multiple lumen, multiple conductor leads according to the present invention can be leads manufactured with smaller diameters, than corresponding multiple lumen leads with circular conductors and lumens. A reduced diameter is desirable for applications in which more than two conductors are required, in order to allow the use of sensors and/or multiple electrodes on a single lead. As an added benefit, leads according to the preferred embodiment of the present invention are easily manufactured, as the limited points of contact between the conductors and the lumens ease insertion of the conductors into the lumens during assembly.

BRIEF DESCRIPTION OF THE DRAWING

Throughout the several figures of the drawing like numerals refer to identical elements throughout, wherein.

DETAILED DESCRIPTION OF THE PREFERRED EMBODIMENT

Figure 1:
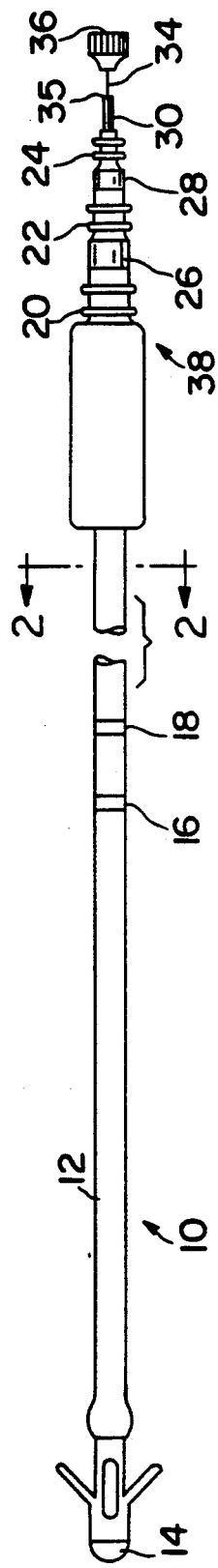
FIG. 1 is a diagram of a lead which incorporates a preferred embodiment of the present invention.

FIG. 1 is a diagram of a lead assembly 10 which incorporates a preferred embodiment of the present invention. The lead assembly 10 is tri-polar and has three electrodes. The tip electrode 14 is located at the distal end of the lead body 12. A first ring electrode 16, and second ring electrode 18 are located proximal to the distal end. If the lead is intended for use as a pacing lead, electrode 14 may be located in the ventricle of a patient's heart and electrodes 16 and 18 located in the atrium. The proximal end of the lead assembly 10 includes a tri-polar in-line connector assembly 38. The in-line connector assembly 38 includes a first connector ring 26, coupled to electrode 18, a second connector ring 28, coupled to ring electrode 16, and a tip connector pin 30, coupled to tip electrode 12. The various connector rings are isolated from each other by sealing ring assemblies shown in the drawing as first sealing ring assembly 20, second sealing ring assembly 22 and third sealing ring assembly 24.

Individual conductors are located within the lead body 12 to couple the electrodes to the appropriate connector ring or pin in the in-line connector assembly 38. The tip connector pin 30 has a stylet receiving aperture 35. The stylet wire 34 may be inserted into the aperture 35 and positioned within the lead by the stylet knob 36. The stylet is used to stiffen and manipulate the lead assembly 10 during implantation.

As illustrated, the lead includes electrodes which may serve as means for delivering stimulation pulses and as means for sensing physiological electrical signals. It should also be understood that a lead according to the present invention may also include one or more means for sensing other physiologic parameters, such as pressure, oxygen saturation, temperature or pH. The lead may include electrodes only, other physiologic sensors only or a mixture of the two. Further, a lead employing only a single sigmoidal conductor and non-circular lumen, for example a unipolar pacing lead, is also within the scope of the present invention.

Figure 2:
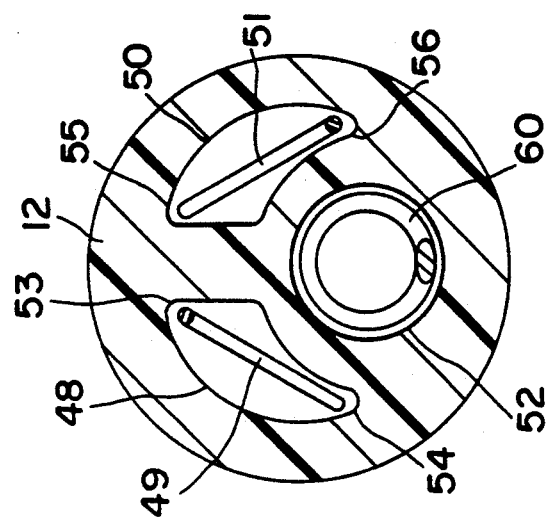
FIG. 2 is a cross-sectional view of a segment of the lead body of the lead shown in FIG. 1; and, FIG. 3 shows a cut-away view of a segment of the lead body.

FIG. 2 is a cross-section of the lead body 12. The lead body may be fabricated of silicone rubber, polyurethane, or other flexible, biostable, biocompatible polymer. This drawing shows a "non-round" first lumen 48 and a "non-round" second lumen 50. Each of the lumens 48, 50 displays a height substantially less than its width, with areas of minimal height located adjacent their edges, 53, 54, 55, 56. As illustrated, the sigmoidal or serpentine conductors 49, 51 each lie generally in a single plane and extend across the width of their respective lumens, 48, 50, contacting the lumens only in areas adjacent the edges thereof. It should be understood that it is preferable that the conductors extend somewhat less than all of the way across the lumens, so that they fit loosely therein.

The drawing also shows a third round lumen 52 formed in the lead body 12. The third lumen may contain a coiled conductor 60, which may serve both as a conductor, connected to an electrode or sensor and as a means for receiving a stylet and preventing the stylet from puncturing the lead body. Alternatively, a plastic tube of Teflon, Kynar, Tefzel or other harder plastic material may be employed to receive the stylet, in the event that fewer conductors are desired.

It should be appreciated that alternative lumen shapes, for example ellipses, are also workable in the context of the present invention. The shape of the conductor and the fact that it lies generally in a single plane permits a wide variety of lumen shapes. Further, while in the preferred embodiment, lumens 48 and 50 each have their width extending generally perpendicular to a radius of the lead body and extending generally parallel to the outer surface of the lead body, other orientations of the lumens relative to the lead body are may also be employed. For example, one or more lumens having their widths extending generally along a radius of the lead body might also be employed.

The lead body may employ the multi-lumen configuration illustrated throughout its length, with lumens 48 and 50 unused distal to electrodes 16 and 18. However, a transition to a lead body having only single round lumen containing a single coiled conductor coupled to electrode 14 may instead occur at or distal to electrodes 16 and 18.

Figure 3:
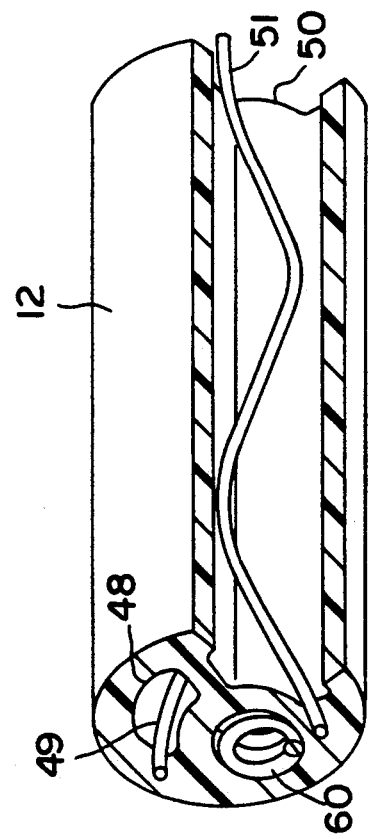

FIG. 3 shows a cut-away view of a segment of the lead body 12, between the connector assembly and ring electrode 18, with the outer wall adjacent lumen 50 removed. This view shows the sigmoidal or serpentine shape of the conductors 49 and 51. In general conductors 49 and 51 are formed into free standing undulating curves which lie substantially in one plane. These formed conductors are then loosely threaded into lumens 48 and 50 formed in the lead body 12.

The conductors' shape and the lumens' shape together result in the conductors making only occasional contact with the inner surfaces of the lumens 48 and 50. In any given cross-section of the lumen, the conductors will exhibit no more than one contact point between the conductors and the inner surfaces of the lumens. The relatively minor areas of contact between the conductors and the lumens allows great freedom of relative movement of the lead body and the conductors with minimal friction, enhancing the flexibility and stretch characteristics of the lead. In addition, because the sigmoidal conductors do not extend any substantial distance across the lumens in any given cross section, there is less potential for damage to the conductors due to localized crushing or compression of the lead body, as might occur, for example, due to excessively tightened sutures at the site of venous insertion.

Experimentation has suggested that an optimum pitch may exist for a serpentine or sigmoidal conductor to maximize flex life of the composite lead. The actual pitch value will depend upon the shape of the lead and the materials and construction of the sigmoidal conductor and must be ascertained empirically for each lead design. However, a gentle, serpentine shape as illustrated is believed to be generally desirable.

The conductors may be formed from twisted strands of wire made from MP-35N nickel cobalt alloy, titanium, tantalum, niobium, platinum, platinum-5 nickel cladded MP-35N or other electrically conductive biocompatible metal. For example, each conductor may comprise seven strands of MP-35N alloy, each with a diameter of about 0.0005 to 0.0030 inches, with six strands wound a central strand at a pitch of 0.30 to 0.60 inches. A coating of a biocompatible polymer such as PTFE may be applied to the outer surface of the strands after winding. Alternatively, bundled, stranded wire as disclosed in the above-cited U.S. Pat. No. 4,964,414, issued to Handa et al and incorporated herein by reference, but formed into serpentine or sigmoidal configurations, may also be employed. Similarly, conductors fabricated of a nickel-titanium alloy as described in the above-cited U.S. Pat. No. 4,608,986, issued to Beranek et al and incorporated herein by reference in its entirety, but formed into serpentine or sigmoidal configurations, might also be employed, provided that the mechanical characteristics claimed for the material are realizable in practice.

Although an illustrative tri-polar lead has been shown it is understood that various changes and modifications may be made therein within the scope of the appended claims without departing from the spirit and scope of my invention.

What is claimed is:

1. A medical electrical lead, comprising:
   an elongated lead body, said lead body having a first lumen extending along the length of said lead body, said lumen in cross section having a width greater than its height;
   a first sigmoidal conductor lying in generally in a first plane and extending along the length of said lead body and across the width of said lumen; and
   first connector means mounted to said lead body and coupled to said first sigmoidal conductor for establishing electrical connection to said first sigmoidal conductor.

2. A lead according to claim 1 further comprising an means for sensing a physiological parameter, mounted to said lead body and coupled to said first sigmoidal conductor.

3. A lead according to claim 1 or claim 2 wherein said lead body has a generally circular cross section and wherein the width of said lumen generally extends perpendicular to a radius of said lead body.

4. A lead according to claim 1 or claim 2, wherein said lead body has a second lumen extending along the length of said lead body and in cross section having a width greater than its height; further comprising;
   a second sigmoidal conductor lying in generally in a second plane and extending across the width of said second lumen; and
   second connector means mounted to said lead body and coupled to said second sigmoidal conductor for establishing electrical connection to said second sigmoidal conductor.

5. A lead according to claim 4 wherein said lead body has a third lumen extending along the length of said lead body and having a generally circular cross section.

6. A lead according to claim 5 further comprising a coiled conductor located within said third lumen.

7. A lead according to claim 5 further comprising means for receiving a stylet, located within said third lumen.

8. A lead according to claim 1 further comprising an electrode, mounted to said lead body and coupled to said first sigmoidal conductor.

9. A lead according to claim 2 wherein said means for sensing a physiologic parameter comprises an electrode, coupled to said first sigmoidal conductor.

10. A medical electrical lead, comprising:
    an elongated lead body, said lead body having a first lumen extending along the length of said lead body, said lumen in cross section having a width greater than its height;
    a first sigmoidal conductor lying in generally in a first plane, said first sigmoidal conductor extending along the length of said lead body and across the width of said lumen;
    a first electrical contact means mounted to said lead body and coupled to said sigmoidal conductor for establishing electrical connection to said first sigmoidal conductor; and
    a second electrical contact means coupled to said sigmoidal conductor, at a point spaced from said first contact means, for establishing electrical connection to said first sigmoidal conductor.

11. A lead according to claim 10, wherein said lead body has a second lumen extending along the length of said lead body and in cross section having a width greater than its height; further comprising;
    a second sigmoidal conductor lying in generally in a second plane, said second sigmoidal conductor extending across the width of said second lumen;
    a third electrical contact means mounted to said lead body and coupled to said sigmoidal conductor for establishing electrical connection to said second sigmoidal conductor; and
    a fourth electrical contact means coupled to said sigmoidal conductor, at a point spaced from said third contact means, for establishing electrical connection to said first sigmoidal conductor.

12. A lead according to claim 11 wherein said lead body has a third lumen extending along the length of said lead body and having a generally circular cross section.

13. A lead according to claim 12 further comprising a coiled conductor located within said third lumen.

14. A lead according to claim 13 further comprising an electrode, mounted to said lead body and coupled to said coiled conductor.

15. A lead according to claim 12 further comprising means for receiving a stylet, located within said third lumen.

16. A lead according to claim 10 or 11 wherein said second contact means comprises means for sensing a physiologic parameter, mounted to said lead body and coupled to said first sigmoidal conductor.

17. A lead according to claim 16 wherein said means for sensing a physiologic parameter comprises an electrode, coupled to said first sigmoidal conductor.

* * * * *